United States Patent [19]

Ball et al.

[11] 4,098,877
[45] Jul. 4, 1978

[54] ANTIMICROBIAL COMPOSITION (ENHANCED ACTIVITY FROM COMBINATION OF PHENOL AND A QUATERNARY COMPOUND)

[75] Inventors: William L. Ball, Kinnelon; Eugene E. Wiese, Wyckoff, both of N.J.

[73] Assignee: American Cyanamid Company, Stamford, Conn.

[21] Appl. No.: 787,825

[22] Filed: Apr. 15, 1977

Related U.S. Application Data

[63] Continuation of Ser. No. 613,659, Sep. 15, 1975, abandoned.

[51] Int. Cl.² .................. A01N 9/02; A01N 9/20; A01N 9/26
[52] U.S. Cl. .................................. 424/45; 424/329; 424/340
[58] Field of Search ................. 424/45, 329, 340

[56] References Cited

U.S. PATENT DOCUMENTS

| | | | |
|---|---|---|---|
| 3,625,903 | 12/1971 | Davies et al. | 252/107 |
| 3,723,326 | 3/1973 | Cheng et al. | 252/107 |
| 3,725,547 | 4/1973 | Kooistra | 424/245 |
| 3,787,566 | 1/1974 | Gauvreau | 424/45 |
| 3,794,587 | 2/1974 | Jungermann | 252/107 |

OTHER PUBLICATIONS

Harry, Cosmetic Materials, vol. Two (1963) pp. 239–241.
McCutcheon's Detergents & Emulsifiers 1971, p. 78.

*Primary Examiner*—Allen J. Robinson
*Attorney, Agent, or Firm*—Charles J. Fickey

[57] ABSTRACT

An antimicrobial composition having improved effectiveness which comprises two known germicidal components, (1) a phenolic bacteriostat and (2) a long-chain alkyl, phenoxyalkyl substituted quaternary bacteriocide where the combination results in surprisingly enhanced disinfectant and antiseptic effect.

4 Claims, No Drawings

ANTIMICROBIAL COMPOSITION (ENHANCED ACTIVITY FROM COMBINATION OF PHENOL AND A QUATERNARY COMPOUND)

This is a continuation, of application Ser. No. 613,659, filed Sept. 15, 1975, now abandoned.

This invention relates to an improved antimicrobial system, comprising a combination of two known germicidal components, which exhibits unexpectedly superior effectiveness, wherein the effectiveness is greater than could have been foreseen from the known activity of each component. It further relates to an improved antimicrobial system containing a phenolic bacteriostat and a quaternary compound bacteriocide, the system being useful for a variety of purposes and in various compositions where a disinfectant and antiseptic action is desired.

Thus, it is an object of the invention to provide an effective antimicrobial system, which may be used in various types of compositions for application to human and animal skin for disinfectant and antiseptic purposes, with non-irritating and non-stinging properties, the system being adaptable for various means of application.

The present invention is based on the combination of a phenolic bacteriostat compound and a long-chain alkyl, phenoxy alkyl substituted quaternary bacteriocide compound, the combination of the two components resulting in a surprisingly enhanced disinfectant and antiseptic effect. The enhanced effect resulting from the combination, greater than the individual effects of the two separate components is unexpected and could not have been predicted from the known properties of the two components although each of the components individually is known to have at least some degree of effectiveness as an antiseptic or a disinfectant.

The phenolic component of the system is dientified as 5-chloro-2-(2,4-dichlorophenoxy)phenol.

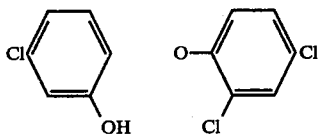

The quaternary component of the compositions of the invention may be represented by the following structure:

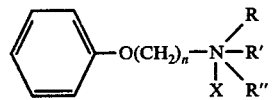

where $n$ is 1 or 2; R and R' are alkyl of 1 or 2 carbon atoms; R" is an alkyl of 10 to 18 carbon atoms; X is a halogen.

Although various quaternary components fall within the above described definition, the preferred compound is dodecyl dimethyl (2-phenoxyethyl)ammonium bromide.

The phenolic component of the composition is a commercially available germicidal compound (bacteriostat) identified as Irgasan DP-300, which is known to be useful, for example in soap compositions. The preferred quaternary compound identified above is a commercially available bacteriocide material sold as Fungitex R.

In general, this invention comprises a combination of 5-chloro-2-(2,4-dichlorophenoxy)phenol and a quaternary compound. The combination of an effective amount of each compound provides a composition which is "synergistic", i.e., more effective as an antimicrobial agent at a lower concentration than either of the two agents taken independently. Thus, higher amounts of either compound are less effective as an antimicrobial. The phenolic component, for example, will not kill the microorganisms, when used in any suspending vehicle of the invention, in 10 minutes, and the quaternary, which has a solubility limit of 0.03% in the preferred suspending vehicle, will not kill in 10 minutes.

In many instances phenolic derivatives and quaternary components are normally not included in the same composition, since it would be expected that at least some degree of inactivation of the potential antimicrobial activity would result.

However, in the compositions of the present invention the combination of the two ingredients results not only in an enhanced antimicrobial activity but a "synergistic" effect is exhibited by the combination.

The compositions of the invention are particularly useful as antimicrobial agents in that they are effective against a very broad spectrum of microorganisms, including both gram positive and gram negative bacteria, in addition to yeasts, such as Candida albicans. Thus, the compositions are effective against common contaminants of the skin wherever located and a maximum beneficial effect is obtained because of the high activity of the compositions.

In the compositions of the invention the ratio of the phenolic component to the quaternary component may vary from about 1:1 to about 10:1. A preferred and practical ratio of the two components is from about 4:1 to 6:1.

Although the antimicrobial system of the invention may be used in various compositions, for practical application they are of particular use in those compositions where water or water and alcohol mixtures are absent. The system can normally be used in various types of formulations as known in the art and by various means of application to the skin of humans and animals, particularly where non-irritating and non-stinging effects are desired; for example: pre-surgical scrub-up for physicians; for pre-operative treatment of the skin; feminine hygiene; underarm deodorizing; etc., or in general disinfectant use, such as in bathroom cleaners.

The system can also be used for various antimicrobial purposes in hair preparations, such as shampoos, in medicated cosmetics, in fungicidal preparations, or in any preparation where disinfectant and antiseptic effectiveness is desired.

For many applications the antimicrobial system may be combined with a known carrier vehicle, preferably containing no water or alcohol. A convenient method of application for such a composition is of course through an aerosol application where the composition is combined with a propellent, or in a deodorant stick.

In such aerosol compositions the active antimicrobial system may be present at a concentration of about 0.01 to 5% with the carrier vehicle being present in a concentration of about 1.0 to 30.0% based on the total composition, which would normally include the propellent.

Conventional carrier vehicles are applicable for these compositions including for example various esters of long chain acids and alcohols, such as isopropyl myristate, lauryl or stearyl myristate, palmitate, stearate, adipate or further branched chain derivatives thereof, etc.; paraffinic solvents such as mineral oil, branched chain hydrocarbons, glycols, glycol ethers, polypropylene and polyethylene glycols, high molecular weight alcohols, such as hexadecyl alcohol, carbitol solvent, etc.

A preferred carrier vehicle is isopropyl myristate or a mixture of fatty esters of the approximate compositions; known as WICKENOL 163.

di(2-ethylhexyl)adipate — 25%
2-ethylhexyl stearate — 41%
2-ethylhexyl palmitate — 34%

When tested alone this does not have antimicrobial activity.

The propellent system where applicable can consist of any halogenated hydrocarbon or mixture thereof, straight hydrocarbon such as isobutane, carbon dioxide, nitrous oxide, or any combination of these. Examples of halohydrocarbons include products available commercially and identified as Freon propellents, such as trichlorofluoromethane, dichlorodifluoromethane, carbon tetrafluoride, 1,2-dichloro-1,1,2,2-tetrafluoroethane, and the like.

The invention is further illustrated by the following examples:

EXAMPLE 1

The antimicrobial activity of a combination of the phenolic component and the quaternary component in a typical formulation was subjected to bacteriological evaluation. For this purpose each individual component was incorporated with a fatty ester carrier vehicle and a combination of the two components was also incorporated in the same vehicle.

Minimum killing and inhibitory concentrations were then determined on three organisms. The minimum killing and/or inhibitory concentration (MIC) will be called Method 1.

The procedure used and results obtained are shown in the following:

Method 1

The following procedure is a standard method used to determine the MIC activity. The medium was A.O.A.C.* nutrient broth and contained 1% peptic hydrolysate of pork tissue; 0.5% NaCl; and 0.5% beef extract. This was dissolved in distilled water and prepared according to methods of analysis - A.O.A.C. Eleventh Edition 1970, Chapter 4, page 59, 4.001 (a) culture media. The bacterial inoculum is prepared by adding one tenth (0.1) ml. of an 18-24 hours, 35°-37° C. bacterial test organism to 99.9 ml. of the above-mentioned nutrient broth (anatone broth). The yeast inoculum is prepared by adding three tenths (0.3) ml. of a 48-hour yeast culture in Sabouraud's broth to 99.7 ml. of Sabouraud's broth.

*Assoc. Official Analytical Chemists

Each material to be tested was prepared as a 1% stock solution. The synergistic stock mixture was composed of 0.5% phenoxy phenol and 0.03% quaternary compound in the suspending fluid. ** One (1) ml. of stock solution is dispensed into the first tube. Then one (1) ml. of the stock solution is added to the second tube containing one (1) ml. of the suspending fluid and mixed. The material in the second tube is serially diluted in the suspending fluid throughout ten (10) tubes. This dilution scheme gives 1000 ppm in the first tube and 1.95 ppm in the tenth tube. Following the ten (10) tube serial dilution, in the suspending fluid, each tube is inoculated with 8.0 ml. of the 0.1% seeded nutrient broth for the bacteria and 0.3% Sabouraud's broth for the yeast. Finally, one (1) ml. of suspending fluid is added to each tube to bring the volume up to ten (10) ml.

** Suspending Fluid Wickenol 163: Dl-(2-Ethyl)Adipate – 25%
2-Ethyl Hexyl Stearate – 41% 2-Ethyl Hexyl Palmitate – 34%

All bacterial tests are incubated at 35°-37° C. for 24 hours and all yeasts are incubated at 32°-35° C. for 48 hours and read for growth (turbidity) or no growth (clear tube). The lowest concentration or highest dilution showing a clear tube is the minimum inhibitory concentration. To obtain cidal or killing dilution, it is necessary to inoculate tubes of A.O.A.C. Letheen Broth 4.001 (c) from clear and turbid tubes in the range of endpoint (minimum inhibitory concentration). Letheen broth is anatone broth plus 0.7% lecithin and 0.5% polysorbate 80 (Tween 80) added as neutralizers for antimicrobial agents (phenolic and quaternary that may carry over). The yeasts are transferred to Sabouraud Broth plus neutralizers.

The results of these tests are in Table I.

Table I

| Sample | S. aureus FDA209 | | | E. coli | | | C. albicans | | |
|---|---|---|---|---|---|---|---|---|---|
| | 1 | 2 | 3 | 1 | 2 | 3 | 1 | 2 | 3 |
| Phenoxy phenol | 0.1% | | 0.0062% | 0.1% | | 0.05% | 0.1% | | 0.05% |
| Quaternary | | 0.0015% | 0.00018% | | 0.3% | 0.0015% | | 0.03% | 0.0015% |
| Results | + | + | − | + | + | − | + | + | − |

− = Indicates no visual microbial growth
+ = Indicates no visual microbial growth inhibition
% = concentration by volume based on weight in oil
Phenoxyphenol = 5-chloro-2-(2,4-dichloro phenoxy) phenol
Quaternary = dodecyl dimethyl (2-phenoxy-ethyl) ammonium bromide

EXAMPLE 2

Seven solutions were prepared in isopropyl myristate as follows:

Table 2

| Soln. No. | % Phenolic Added | % Phenolic in solution (by Analysis) | % Quat. Added | Quaternary in solution (by Analysis) | Ratio Phenolic/Quaternary |
|---|---|---|---|---|---|
| 1 | 7.14 | 7.63 | 7.14 | 1.38 | 5.5 |
| 2 | 8.57 | 8.78 | 5.71 | 1.88 | 4.6 |
| 3 | 11.43 | 11.64 | 2.86 | 2.79 | 4.0 |
| 4 | 12.86 | 13.14 | 1.43 | 1.33 | 9.67 |
| 5 | 6.67 | 6.68 | 6.67 | 6.72(1) | 1.0 |
| 6 | 7.69 | 7.68 | 0 | — | — |
| 7 | 0 | — | 7.69 | 0.03(2) | — |

(1)6.67 SD-40 Anhydrous ethanol added
(2)max. solubility at 22° C.

The solutions were filtered and diluted 1:100 with isopropyl myristate (Note: solution No. 7 was not diluted since 0.3% or 3000 ppm is the maximum concentration of quaternary in isopropyl myristate.) The other solutions were diluted to bring them into a practical disinfectant concentration range.

Using A.O.A.C. Methods of analysis - Eleventh Edition 1970, page 60 (4.003) Phenol coefficient technique, the following critical time kill data can be generated. Actually, 4.5 ml. of isopropyl myristate containing antimicrobials are inoculated with 0.5 ml. of 24 hours cultures of S. aureus (GRAM +), *Salmonella choleraesuis* (GRAM −), and *Candida albicans* (yeast) and incubated at 20° C. Samples are taken after 5, 10 and 15 minutes contact.

As one can note in Tables 3, 4, and 5, solution 6 (DP-300 only) and solution 7 (Fungitex R only) do not kill in 15 minutes. However, solutions 1 to 5 kill all three organisms in 10 minutes. This data not only demonstrates synergism for these compositions but indicates hard surface disinfectant, as well as skin disinfectant activity. Products of this or similar composition for example could be used as hard surface disinfectants, cleaner disinfects, polishes, as well as waterless hand cleaners.

Note: In combinations of the invention the presence of the phenolic permits increased solubility of the quaternary in the suspending vehicle.

Table 3

Critical Time Kill Data

The bactericidal solutions are those which kill in 10 minutes but not in 5 minutes, according to the AOAC Phenol Coefficient Procedure.

| Solution No. | *Salmonella choleraesuis* - ATCC 10708 | | | Phenolic/Quat. Ratios |
|---|---|---|---|---|
| 1:100 Dilution | 5 Min. | 10 Min. | 15 Min. | |
| 1 | + | − | − | 5.5/1 |
| 2 | + | − | − | 4.6/1 |
| 3 | + | − | − | 4.0/1 |
| 4 | + | − | − | 9.67/1 |
| 5 | + | − | − | 1-1 |
| 6 | + | + | + | − |
| 7 (not diluted) | + | + | + | − |

+ = Indicates visual microbial growth
− = Indicates no visual microbial growth

Table 4

| Solution No. | *Staphylococcus aureus* FDA 209, ATCC 6538 | | | Phenolic Quat. ratios |
|---|---|---|---|---|
| 1:100 Dilution | 5 Min. | 10 Min. | 15 Min. | |
| 1 | + | − | − | 5.5/1 |
| 2 | + | − | − | 4.6/1 |
| 3 | + | − | − | 4.0/1 |
| 4 | + | − | − | 9.67/1 |
| 5 | + | − | − | 1/1 |
| 6 | + | + | + | |
| 7 | + | + | + | |

Table 5

| Solution No. | *Candida albicans* | | | Phenolic Quat. Ratios |
|---|---|---|---|---|
| 1:100 Dilution | 5 Min. | 10 Min. | 15 Min. | |
| 1 | − | − | − | 5.5/1 |
| 2 | − | − | − | 4.6/1 |
| 3 | − | − | − | 4.0/1 |
| 4 | − | − | − | 9.67/1 |
| 5 | − | − | − | 1/1 |
| 6 | + | + | + | |
| 7 | + | + | + | |

What is claimed is:

1. A composition having disinfectant and antiseptic activity comprising an effective amount of the mixture of 5-chloro-2-(2,4-dichlorophenoxy)phenol and dodecyl dimethyl(2-phenoxyethyl)ammonium bromide, the ratio of phenolic compound to ammonium bromide compound being about 4:1 to 6:1.

2. A composition as in claim 1 where the composition is combined with a fatty ester vehicle.

3. A composition as in claim 2 where the vehicle is isopropyl myristate.

4. A composition as in claim 2 in combination with an aerosol propellant.